United States Patent [19]

Weidenbach et al.

[11] Patent Number: 4,533,633

[45] Date of Patent: Aug. 6, 1985

[54] PROCESS AND APPARATUS FOR ISOMERIZING GLUCOSE TO FRUCTOSE

[75] Inventors: Günter Weidenbach, Hanover; Dirk Bonse, Arpke/Lehrte; Boris Meyer, Hanover, all of Fed. Rep. of Germany

[73] Assignee: Kali-Chemie Aktiengesellschaft, Hanover, Fed. Rep. of Germany

[21] Appl. No.: 422,296

[22] Filed: Sep. 23, 1982

[30] Foreign Application Priority Data

Dec. 9, 1981 [DE] Fed. Rep. of Germany ....... 3148603

[51] Int. Cl.$^3$ ...................... C12P 19/24; C12N 11/14; C12M 1/40

[52] U.S. Cl. ...................... 435/94; 435/176; 435/288

[58] Field of Search .................. 435/94, 176, 288; 127/46.2, 55

[56] References Cited

U.S. PATENT DOCUMENTS

| | | |
|---|---|---|
| 4,014,711 | 3/1977 | Odawara et al. ................ 127/46 B |
| 4,040,861 | 8/1977 | Walon ................ 127/46.2 |
| 4,100,025 | 7/1978 | Enokizono et al. ........... 127/46.2 X |
| 4,226,639 | 10/1980 | Michalko et al. ................ 127/55 X |
| 4,230,803 | 10/1980 | Weidenbach et al. .............. 435/176 |
| 4,288,548 | 9/1981 | Barrett et al. ........................ 435/94 |
| 4,373,025 | 2/1983 | Neuzil et al. ......................... 435/94 |

FOREIGN PATENT DOCUMENTS 1539680 1/1979 United Kingdom.

*Primary Examiner*—David M. Naff
*Attorney, Agent, or Firm*—Schwartz, Jeffery, Schwaab, Mack, Blumenthal & Evans

[57] ABSTRACT

When isomerizing part of the glucose content of a glucose-containing solution to fructose, the productivity of glucose isomerase immobilized on an $SiO_2$ carrier is increased considerably by pre-contacting the glucose-containing solution with particles of $SiO_2$ or aluminum silicate. An apparatus is used having a reaction vessel containing the immobilized glucose isomerase and a pre-column containing the particles of $SiO_2$ or aluminum silicate.

25 Claims, 3 Drawing Figures

PROCESS AND APPARATUS FOR ISOMERIZING GLUCOSE TO FRUCTOSE

BACKGROUND OF THE INVENTION

The present invention pertains to a process for the preparation of a solution containing glucose and fructose by the conversion of a glucose-containing solution in the presence of a catalyst having glucose isomerase activity which is prepared based on a $SiO_2$ carrier.

The enzymatic conversion of glucose into a glucose-fructose mixture has recently taken on a greater significance. The mixture is sold most often in the form of a syrup, called isomerose, and serves as a replacement, above all, in the food and beverage industry, for crystal sugar which worldwide is becoming less abundant and more expensive, i.e., sugar such as cane sugar, beet sugar and saccharose which are produced from sugar cane or sugar beets. As a source for the glucose which is required for the production of the glucose-fructose mixture, there serve naturally available starches, e.g., corn starch, or potato starch, which are converted into glucose by acidic and/or enzymatic hydrolysis.

The enzymatic conversion of glucose into fructose by means of glucose isomerase is well known in the art. The isomerization can be effected by treating an aqueous glucose solution with a glucose isomerase, whereby depending on the type of glucose isomerase additional agents which promote isomerization (e.g. cofactors such as cobalt and/or magnesium ions) may be added to the solution. The solution is subjected to the effect of the glucose isomerase until the desired degree of isomerization is achieved, then optionally any added ingredients may be removed from the solution and the solution may be concentrated to form a syrup.

In the past, it was conventional to operate in a batchwise manner and to use either isolated glucose isomerase or glucose isomerase left in the natural cellular association of the micro-organism which produces the glucose isomerase. In view of the fact that glucose isomerase utilized in this form either cannot at all or can only at considerable expense be recovered and reutilized, more recently it is becoming more common to utilize glucose isomerase which is made water-insoluble by fixation in the cellular association and which is mechanically stabilized by appropriate additives. Furthermore, glucose isomerase can be adsorptively or covalently bound on inorganic or organic carriers and can thereby be made water-insoluble. A glucose isomerase which in this manner is fixed and stabilized or is bonded to a carrier can be reutilized several times. Thus it becomes possible to operate in a continuous manner for example, in a process whereby the carrier-bonded glucose isomerase is filled into a reactor and the glucose solution (i.e., the substrate) is permitted to flow through the reactor.

The carrier-bonded glucose isomerase which is necessary for such a continuous process (hereinafter referred to as a catalyst or a supported catalyst having glucose isomerase activity) forms a part of the state of the art. For example, see U.S. Pat. No. 4,230,803, which describes in particular a catalyst having glucose isomerase activity which is prepared based on a $SiO_2$ carrier.

SUMMARY OF THE INVENTION

It is therefore an object of the present invention to provide an improved process for the at least partial enzymatic conversion of the glucose content of an aqueous glucose solution and for the preparation of isomerose.

In particular, it is an object of the present invention to provide an improvement of an enzymatic conversion process for the preparation of a glucose- and fructose-containing solution wherein a glucose solution (the substrate) flows through a reactor which contains a supported catalyst having glucose isomerase activity and comprising a $SiO_2$-containing carrier.

In particular it is an object of the present invention to provide such an improvement whereby the life time of the supported catalyst is increased.

It is also an object of the present invention to provide an improved apparatus for carrying out the process according to the invention.

In accomplishing the foregoing objects, there has been provided according to the present invention a process for the preparation of a solution containing glucose and fructose, comprising the steps of contacting a glucose-containing solution with particles comprised of $SiO_2$ or aluminum silicate; and thereafter, converting glucose contained in said solution to fructose in the presence of a catalyst having glucose isomerase activity, wherein the catalyst comprises a glucose isomerase immobilized on a $SiO_2$-containing carrier.

According to another aspect of the invention, there has been provided an apparatus for carrying out the process according to the invention, comprising a reactor vessel containing the catalyst, and a precolumn connected to the inlet of the reactor vessel and containing the particles of $SiO_2$ or aluminum silicate.

Further objects, features and advantages of the present invention will become apparent to those skilled in the art based upon the detailed description of preferred embodiments which follows when considered together with the attached figures of drawing.

DETAILED DESCRIPTION OF PREFERRED EMBODIMENTS

Figure 1:
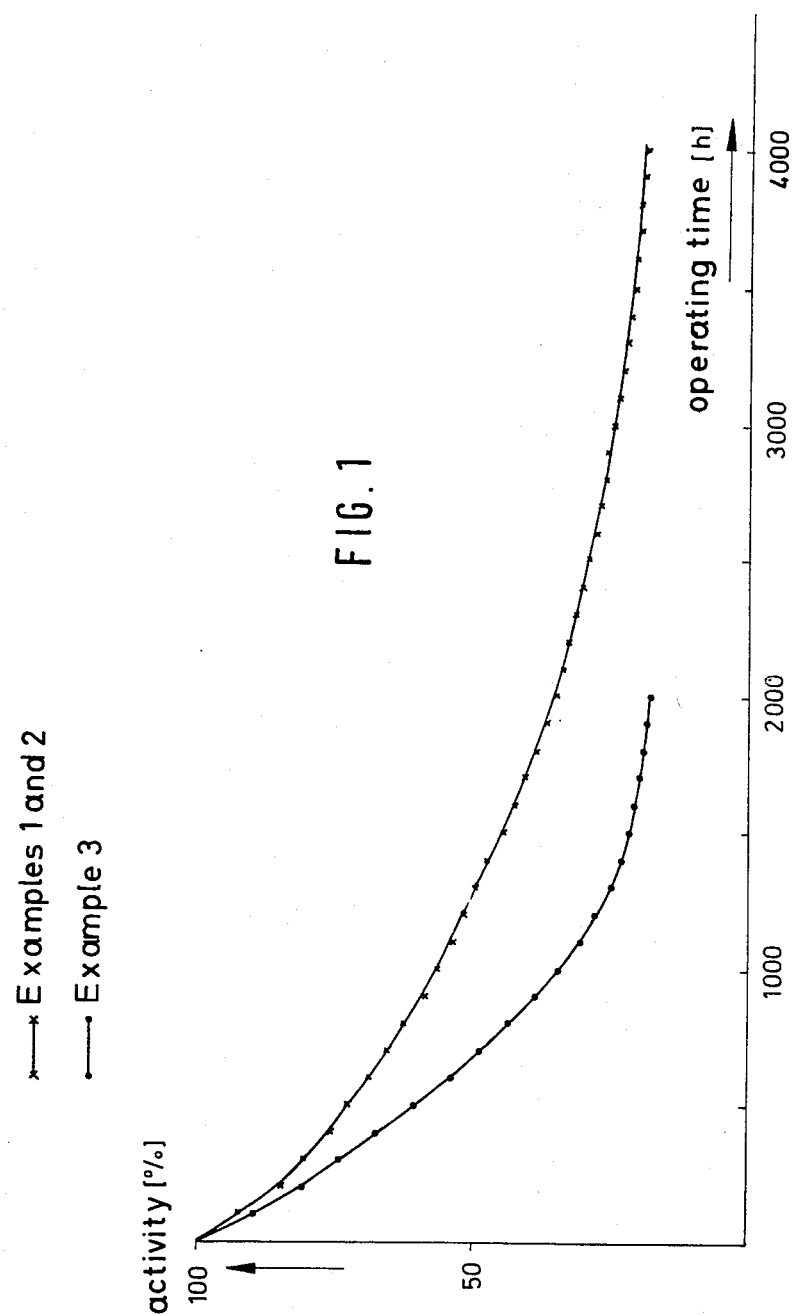
FIG. 1 is a graphical representation of the catalyst activity plotted against the operating time.

The competitiveness of the isomerose in comparison to natural saccharose is depending in part on its price but mainly on its fructose content, since this factor is determinative of its sweetening power. In contrast to natural saccharose, which is a disaccharide of glucose and fructose in which glucose and fructose are present in a molar ratio of 1:1, the content of glucose and fructose in the isomerose, and thus its sweetening power, is not constant. It is primarily dependent upon the period of time for which the glucose solution is subjected to the action of the glucose isomerase and upon the temperature at which the action takes place. The thermodynamic equilibrium which is achievable maximally at 60° C. and which appears after a sufficiently long period of action resides at a degree of isomerization of approximately 51%, i.e., out of 100 molecules of glucose introduced 51 molecules are converted into fructose. Today, the market has accepted an isomerose having a fructose content of 42 weight-% in the dry substance. Since the glucose contents of the industrially used starting materials are as a rule between 90 and 95 weight-%, a degree of isomerization between about 44 and 47% is required as a practical matter, in order to produce this fructose content. In order to achieve a degree of isomerization of this magnitude, it is necessary to utilize the supported catalyst having glucose isomerase activity at a specific space velocity which is dependent upon the respective activity of the catalyst. Modern, highly active catalysts, such as those, for example, which are producible in accordance with the process of U.S. Pat. No. 4,230,803, the disclosure of which is incorporated herein by reference, can be utilized with a beginning space velocity of approximately 10 to 20 v/vh. However, with increasing operating time, the activity of the known catalysts decreases more or less quickly depending upon the reation temperature.

The known catalyst according to U.S. Pat. No. 4,230,803 still maintains 50% of its beginning activity after approximately 670 hours of operation at a reaction temperature of 60° C. In order to achieve the same degree of isomerization as at the beginning of the reaction the space velocity, with which the catalyst is operated, has to be reduced according to the decrease of catalyst activity, that is after 670 hours the catalyst can be utilized at only half of the beginning space velocity. A residual activity of 20%, which is considered the lower limit for economical operation, is reached after 1700 hours of operation.

Surprisingly, it has now been discovered in accordance with the present invention that the operating life time of a supported catalyst having glucose isomerase activity which comprises glucose isomerase on a $SiO_2$ based carrier can be more than doubled, if, prior to the conversion reaction in the presence of the supported catalyst, the glucose-containing solution is contacted with particles or formed bodies comprised of $SiO_2$ or aluminum silicate. Advantageously, the weight ratio of catalyst:particles resides between about 3:1 and 1:3, and preferably at approximately 1:1. As a result of this mode of operation, the productivity of the catalyst is also doubled. The productivity is defined as the amount of substrate, calculated as dry substance (kg), which can be processed at a given degree of isomerization by 1 kg of catalyst until the catalyst activity has decreased to a residual activity of 20% of the beginning activity.

Figure 3:
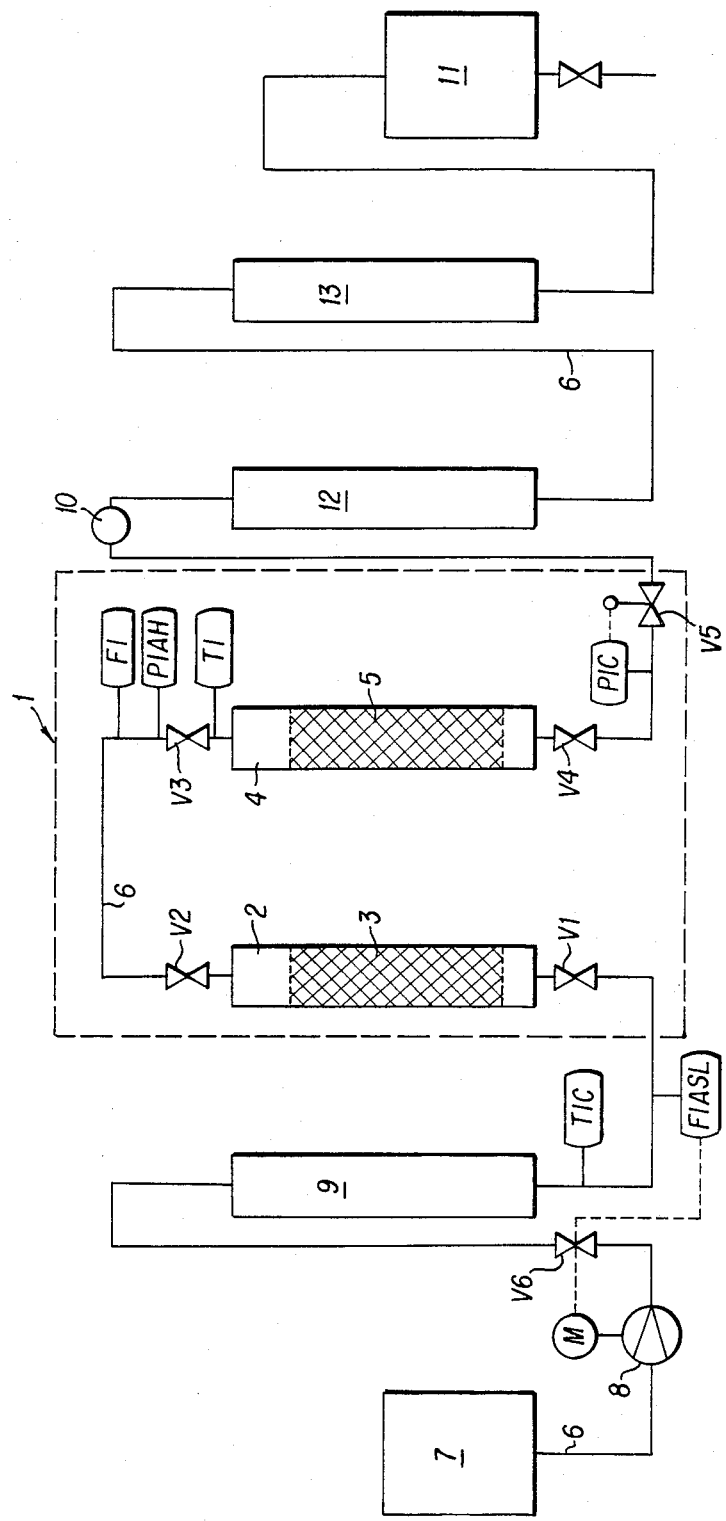
FIG. 3 is a schematic illustration of the apparatus for carrying out the process according to the present invention.

A schematic view of an isomerization assembly according to the present invention is given in FIG. 3.

The isomerization apparatus according to the present invention comprises an isomerization unit (1) comprising a precolumn (2) having an inlet and an outlet for the reaction solution and containing a filling (3) of particles of $SiO_2$ or aluminum silicate, preferably having a particle size of from about 0.5 to about 5.0 mm; a reactor vessel (4) having an inlet and an outlet for the reaction solution and containing a catalyst (5) comprising a glucose isomerase immobilized on a $SiO_2$-containing carrier and preferably having a particle size of from about 0.08 to about 0.5 mm, whereby the per weight ratio of filling in the precolumn to catalyst in the reactor vessel is from about 3:1 to about 1:3, preferably about 1:1; and a conduit-pipe (6) leading to the inlet of the precolumn, connecting the outlet of the precolumn to the inlet of the reactor vessel and leading away from the outlet of the reactor vessel. The conduit-pipe may be further provided with valves (V1-V5) for regulating the flow rate of the reaction solution through the isomerization unit, and/or for easy interuption during exchangement and refilling of precolumn and reactor vessel, a flow indicator (FI), a temperature indicator (TI), and a first pressure indicator (PIAH) which may be adapted to give an alarm signal when the pressure reaches a given upper limit; each of the beforementioned indicators being positioned before the inlet of the reactor vessel; and a second pressure indicator (PIC) positioned after the outlet of the reactor vessel which may be adapted to control valve V5 in order to maintain sufficient pressure in the reactor vessel e.g. to avoid formation of gas bubbles.

Typically an isomerization assembly may comprise the following elements which are connected to each other by means of a conduit-pipe (6) through which the reaction solution is pumped:

A storage tank (7) for storing the glucose solution,
a pump (8) for pumping the solution through the assembly, which pump may be a metering pump,
a heater (9) for heating the glucose solution to the desired reaction temperature, optionally with an inlet valve (V6) positioned before the heater, and optionally positioned behind the heater a temperature control indicator (TIC) and/or a flow indicator (FIASL) which may be provided with an alarm switch low system and may be connected with the inlet valve (V6) and/or the metering pump (8);
the above described isomerization unit (1);
means (10) for removing samples of the partially isomerized solution for analysis and/or analyzing means for determining the fructose content of the solution, which analyzing means may comprise means for polarimetric determination or means for HPL-chromotographic determination;
a receiving tank (11) for collecting the isomerized solution;
and optionally positioned before the receiving tank
a cation exchanger (12) and
an anion exchanger (13) for removing unwanted ionic components.

In carrying out the process of the present invention in a continuous manner in an isomerization apparatus according to the present invention, an aqueous glucose solution, preferably comprising from about 40 to about 50% by weight of dry substance and having a pH of from about 7 to about 8.5 is pumped by means of a metering pump from a storage tank into a preheater where it is heated to the desired reaction temperature, preferably to a temperature of from about 55° to about 65° C. The heated solution then is passed through the isomerization unit passing first through the precolumn containing the particles of $SiO_2$ and/or aluminum silicate and subsequently through the reactor vessel containing the catalyst having glucose isomerase activity. Suitable a catalyst comprising glucose isomerase derived from a *streptomyces albus* is used and as cofactors there are added to the glucose solution Co-II-ions, preferably in an amount of from about 0.1 to about 2 ppm, and Mg-II-ions, preferably in an amount of from about 10 to about 200 ppm. The Co-II ions and the Mg-II ions may be added in the form of watersoluble inorganic salts such as chlorides or sulfates. Furthermore it is advisable to add a stabilizing amount of an antioxidant agent, preferably $SO_2$ which is added in the form of an alkalimetal sulfite or bisulfite, suitably in an amount corresponding to from about 100 to about 600 ppm $SO_2$.

The solution leaving the isomerization unit of the apparatus is analysed and its fructose content determined in a manner known per se.

The flow rate of the solution through the apparatus is adjusted such that the resulting isomerized solution has a fructose content of at least 42% by weight of dry substance. In addition to the flow rate of the substrate, the temperature of the substrate and the operating pressure are controlled and maintained at a given value.

The isomerized solution (=isomerose syrup) is passed on into the receiving tank, where it may be stored. If desired, prior to being introduced into the receiving tank the solution may be purified by passing through a cation exchanger and an anion exchanger, in order to remove any undersirable ionic components e.g. components which adversely affect the taste of the isomerose.

The present invention will now be described in more detail with reference to the following examples which are intended to be merely illustrative.

EXAMPLE 1

5 g of a supported catalyst having glucose isomerase activity, produced according to U.S. Pat. No. 4,230,803 using glucose isomerase derived from *streptomyces albus* and having the properties described below, are filled into the reactor vessel of an isomerization unit according to the above described isomerization apparatus. The precolumn, which is connected to the inlet side of the reactor vessel is filled with 5 g of a commercially available, spherical, water-resistant porous aluminum silicate (e.g., type KCT-WS of Kali-Chemie AG; composition approximately 97 weight percent $SiO_2$ and 3 weight percent $Al_2O_3$). A glucose solution heated to 60° C. and containing the cofactors listed below is pumped through the isomerization unit passing first through the precolumn and subsequently through the reactor vessel. The space velocity (based on the reactor volume required by the catalyst) is adjusted such that the degree of isomerization remains constant at 46.5% over the entire period of operation. The degree of isomerization of the substrate solution exiting the reactor is measured polarimetrically. In particular, the catalyst, pre-column filling and process are characterized by the following parameters:

| 1. Catalyst | |
|---|---|
| 1.1 Carrier: | $SiO_2$ |
| 1.2 Particle size: | 0.1–0.2 mm |
| 1.3 Bulk density (dry): | 0.45 kg/l |
| 1.4 Activity | 9000 U/g |

DEFINITION OF THE ACTIVITY UNIT

One activity unit (U) is defined as the glucose isomerase activity which corresponds to the activity of the amount of enzyme which produces 1 mg fructose under the following incubation conditions. (see also Y. Takasaki: 30 *Agr. Biol. Chem.*, No. 12, 1247–1253, 1966 and Z. Dische and E. Borenfreund: 192 *J. Biol. Chem.*, 583, 1951).

| Incubation conditions: | |
|---|---|
| Temperature: | 65° C. |
| Reaction time: | 1 h |
| Substrate: | 0.1 m glucose × $H_2O$ (Merck 8342) in 0.05 m phosphate buffer, pH 8.0 containing 0.0004 m $MgSO_4$ |
| 2. Pre-column filling | |
| 2.1 Filling material: | KCT-WS (Kali-Chemie AG) |
| 2.2 Particle size: | 1–2 mm |
| 2.3 Bulk density (dry): | 0.70 kg/l |
| 3. Process | |
| 3.1 Substrate: | an aqueous glucose solution containing 45 weight percent glucose |
| 3.2 Co-factors | 120 ppm Mg (II) 1 ppm Co (II) 200 ppm $SO_2$ (in the form of $Na_2SO_3$) |
| 3.3 pH-value: | 7.5 |
| 3.4 Substrate density: | 1.2 kg/l |
| 3.5 Substrate entering temperature: | 60° C. |
| 3.6 Degree of isomerization: | 46.5% |
| 3.7 Beginning space velocity: | 13.0 $h^{-1}$ |

The following results are obtained:

| | |
|---|---|
| Half life of catalyst: | 1,300 h |
| Period of operation to 20% residual activity: | 3,800 h |
| Average activity over 3,800 h operating period: | 44.0% (based on beginning activity of 100%) |
| Productivity after 3,8000 h: | 26,000 kg dry substance containing 46.5 weight % fructose/kg catalyst |

EXAMPLE 2

5 g of a supported catalyst corresponding to Example 1 are filled into the reactor vessel of an isomerizing apparatus. The precolumn which is connected to the inlet side of the reactor vessel contains 10 g of a commercially available spherical, water-resistant, porous $SiO_2$ (e.g., type AF 125 of Kali-Chemie AG, $SiO_2$-content greater than 99 weight percent). The process is carried out as in Example 1. The filling in the precolumn is characterized by the following parameters:

| | |
|---|---|
| 1. Filling material | AF 125 (Kali-Chemie AG) |
| 2. Particle size: | 1–2 mm |
| 3. bulk-density (dry): | 0.45 kg/l |

The results are identical with those of Example 1.

EXAMPLE 3

For the purpose of comparison, Example 1 is repeated with the same catalyst, but without the precolumn; however, the process conditions are otherwise the same. Example 3 produces the following results:

| | |
|---|---|
| Half life of catalyst: | 670 h |
| Period of operation to 20% residual activity: | 1,700 h |
| Average activity over 1,700 h operating period: | 47.2% (based on beginning activity of 100%) |
| Productivity after 1,700 h: | 12,500 kg dry substance containing 46.5 weight % fructose/kg of catalyst |

To illustrate the results according to Examples 1, 2 and 3, the decrease in catalyst-activity as a function of the operating time is plotted in FIG. 1. In this representation, one can clearly see the stabilization of the activity of the catalyst over a long operating period which is achieved by the use according to the invention of the pre-column filled with aluminum silicate- or $SiO_2$-spheres.

Figure 2:
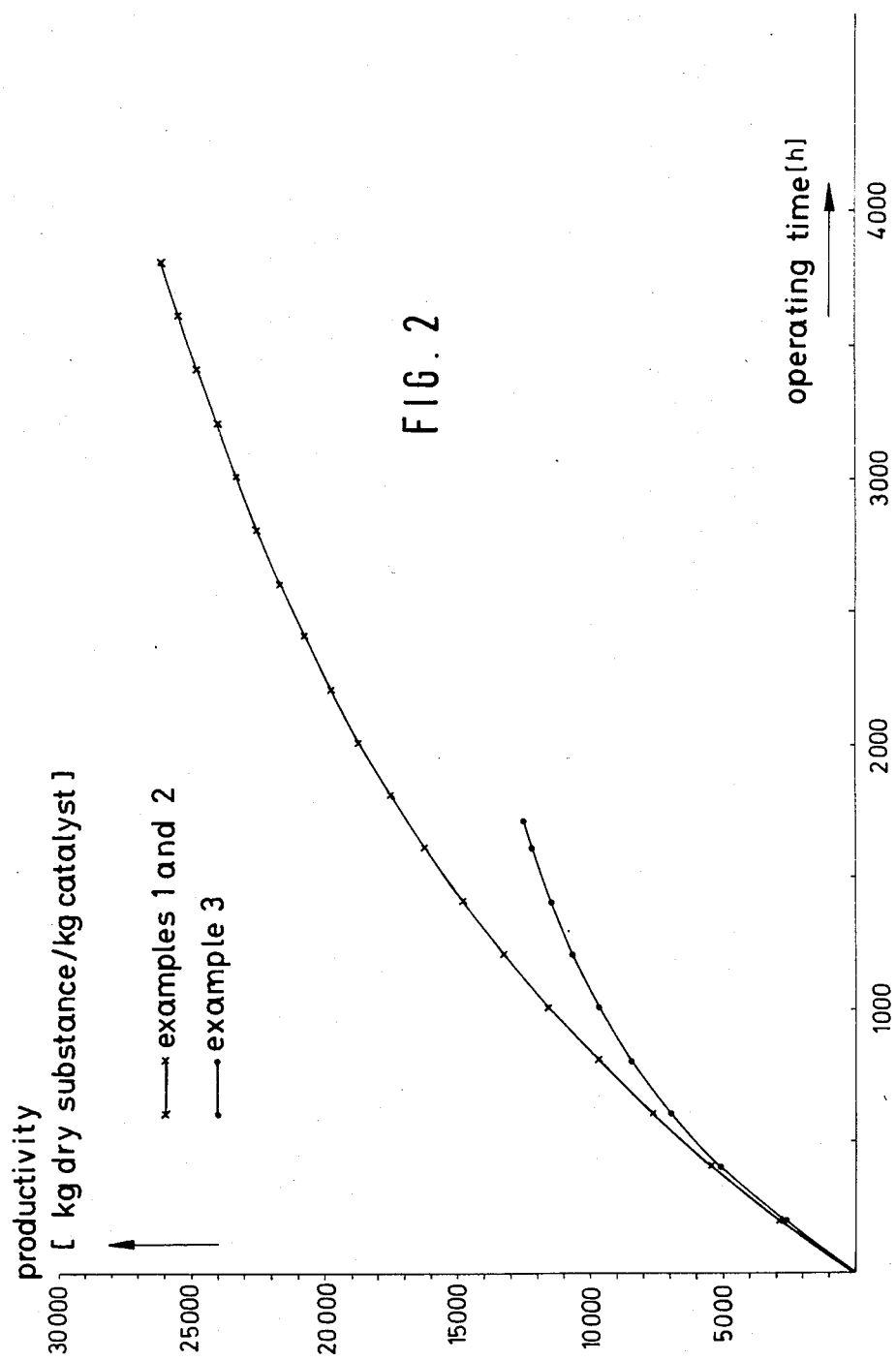
FIG. 2 is a graphical illustration of the productivity plotted as a function of the operating time.

In FIG. 2 is illustrated the development of the productivity of the catalyst as a function of the operating period which is decisive for the economy of the process. Examples 1 and 2, which are carried out under the process conditions according to the invention, raise the economically useful specific performance of the catalyst by a factor of 2.08, i.e., in order to produce a given amount of isomerose, only somewhat less than half the amount of catalyst is needed. The economic advantage of the process according to the invention is considerable, since the material used to fill the pre-column costs only a fraction of the costs of catalyst.

What is claimed is:

1. A process for the preparation of a solution containing a glucose and fructose, comprising the steps of:
   (a) contacting a glucose-containing solution with porous particles consisting essentially of $SiO_2$ or aluminum silicate; and
   (b) thereafter, converting glucose contained in said solution to fructose by contacting the glucose-containing solution with a catalyst having glucose isomerase activity, said catalyst consisting essentially of glucose isomerase attached to a carrier comprising porous particles consisting essentially of $SiO_2$, wherein the weight ratio of catalyst in said contacting step (b): particles in said contacting step (a) is between about 3:1 and 1:3.

2. A process according to claim 1, wherein the weight ratio of catalyst:particles is about 1:1.

3. A process according to claim 1, wherein the particle size of said $SiO_2$ or aluminosilicate particles range from about 0.5 to about 5 mm.

4. A process according to claim 1, wherein the particle size of said catalyst ranges from about 0.08 to about 0.5 mm.

5. A process according to claim 1, wherein said glucose-containing solution comprises from about 40 to about 50% by weight of glucose based on dry substance.

6. A process according to claim 1, wherein the pH of the glucose-containing solution ranges from about 7 to about 8.5.

7. A process as claimed in claim 1, further comprising the step of preheating the glucose-containing solution prior to said contacting step.

8. A process as claimed in claim 7, wherein the temperature of said preheating step ranges from about 55° to about 65° C.

9. A process as claimed in claim 1, wherein said glucose solution further comprises Co-II-ions.

10. A process as claimed in claim 9, wherein the amount of said Co-II-ions ranges from about 0.1 to about 2 ppm.

11. A process as claimed in claim 1, wherein said glucose solution further comprises Mg-II-ions.

12. A process as claimed in claim 11, wherein the amount of said Mg-II-ions ranges from about 10 to about 200 ppm.

13. A process as claimed in claim 9, wherein said Co-II-ions are added in the form of a water-insoluble salt.

14. A process as claimed in claim 13, wherein said water-insoluble salt is selected from the group consisting of chlorides and sulfates.

15. A process as claimed in claim 1, further comprising adding a stabilizing amount of an antioxidant agent.

16. A process as claimed in claim 15, wherein said antioxidant agent comprises $SO_2$.

17. A process as claimed in claim 15, wherein said stabilizing amount ranges from about 100 to about 600 ppm.

18. A process as claimed in claim 1, further comprising the step of providing a flow rate of the solution in said converting step sufficient to produce an isomerized solution having a fructose content of at least about 42% by weight of dry substance.

19. A process as claimed in claim 11, wherein said Mg-II-ions are added in the form of a water-insoluble salt.

20. A process as claimed in claim 19, wherein said water-insoluble salt is selected from the group consisting of chlorides and sulfates.

21. Apparatus for carrying out a process for the preparation of a solution containing glucose and fructose from a starting solution containing glucose, comprising a reactor vessel containing a catalyst consisting essentially of glucose isomerase attached to a carrier comprising porous particles consisting essentially of $SiO_2$, and a pre-column connected to the inlet of said reactor vessel and containing porous particles consisting essentially of $SiO_2$ or aluminum silicate the weight ratio of catalyst in the reactor vessel:particles in the pre-column being between about 3:1 and 1:3.

22. An apparatus according to claim 21, further comprising a preheater for heating said glucose-containing solution prior to entry into said pre-column.

23. An apparatus according to claim 21, further comprising means for measuring the fructose concentration of the solution leaving said reactor vessel.

24. An apparatus according to claim 21, further comprising a purification means comprising a cation and an anion exchanger located downstream from said reactor vessel.

25. An apparatus according to claim 21, further comprising:
   means for supplying said glucose-containing solution to said pre-column;
   a preheater for heating said glucose-containing solution prior to entry into said pre-column;
   means for measuring the fructose concentration of the solution leaving said reactor vessel;
   purfication means for removing ionic components comprising a cation and an anion exchanger located downstream from said reactor vessel; and
   a receiving means for collecting the resulting solution exiting from said purification means.

* * * * *

UNITED STATES PATENT AND TRADEMARK OFFICE
CERTIFICATE OF CORRECTION

PATENT NO. : 4,533,633
DATED : Aug. 6, 1985
INVENTOR(S) : WEIDENBACH et al.

It is certified that error appears in the above—identified patent and that said Letters Patent is hereby corrected as shown below:

IN THE CLAIMS:

Column 8, Claim 13, line 2, kindly delete "water-insoluble" and insert instead -- water-soluble --.
Column 8, Claim 14, line 2, kindly delete "water-insoluble" and insert instead -- water-soluble --.
Column 8, Claim 19, line 2, kindly delete "water-insoluble" and insert instead -- water-soluble --.
Column 8, Claim 20, line 2, kindly delete "water-insoluble" and insert instead -- water-soluble --.

Signed and Sealed this

Fourth Day of February 1986

[SEAL]

Attest:

DONALD J. QUIGG

Attesting Officer

Commissioner of Patents and Trademarks